United States Patent [19]

Myers et al.

[11] Patent Number: 4,880,120

[45] Date of Patent: Nov. 14, 1989

[54] PLASTIC CONTAINER INSPECTION PROCESS

[75] Inventors: Michael J. Myers, Lawrenceville, Ga.; Warren J. Harwick, Milwaukee, Wis.

[73] Assignee: The Coca-Cola Company, Atlanta, Ga.

[21] Appl. No.: 229,839

[22] Filed: Aug. 8, 1988

Related U.S. Application Data

[63] Continuation-in-part of Ser. No. 92,003, Sep. 2, 1987.

[51] Int. Cl.$^4$ .......................... B07C 5/02; B07C 5/34; G01N 33/00
[52] U.S. Cl. .......................................... 209/3.1; 73/23; 73/863.91; 209/523
[58] Field of Search ................. 209/3.1, 509, 522–524, 209/552, 555, 556, 558, 576, 651–654, 644; 73/23, 24, 863.91, 863.92; 250/372, 373; 15/304

[56] References Cited

U.S. PATENT DOCUMENTS

| 2,255,615 | 9/1941 | Frankel ................................ 15/304 |
| 2,901,625 | 8/1959 | Friedman et al. .............. 250/372 X |
| 3,266,292 | 8/1966 | Bailey ...................................... 73/23 |
| 3,321,954 | 5/1967 | Bailey ...................................... 73/23 |
| 3,489,523 | 1/1970 | Claroy et al. .................... 73/23 UX |
| 3,490,267 | 1/1970 | Gordon .................................. 73/23 |
| 3,516,108 | 6/1970 | Loeffler ............................... 15/304 |

Primary Examiner—Dennis H. Pedder
Assistant Examiner—Edward M. Wacyra
Attorney, Agent, or Firm—Eduardo M. Carreras; W. Dexter Brooks

[57] ABSTRACT

A container inspection process and apparatus is provided for detecting the presence of contaminants present on or absorbed into the walls of plastic containers. The process flushes volatiles from within the container by injecting gas, draws a vapor sample from within the container and analyzes the sample by ionization techniques.

13 Claims, 2 Drawing Sheets

PLASTIC CONTAINER INSPECTION PROCESS

CROSS REFERENCE TO RELATED APPLICATION

This application is a continuation-in-part of pending application Ser. No. 07/092,003, filed Sept. 2, 1987, having the same title as this case.

BACKGROUND OF THE INVENTION

1. Field of the Invention

This invention relates to a container inspection process for detecting the presence of contaminants in plastic containers. More specifically, this invention relates to identifying plastic containers which have organic compounds present on or absorbed into the walls of such containers by analyzing the vapors therein.

2. Description of the Prior Art

Plastic containers, such as polyethylene terephthalate (PET) bottles, have long been used for the packaging of carbonated and noncarbonated beverages. Typically, these containers are only used once and then discarded. However, in certain geographic areas, such as central Europe, multiple use containers dominate the beverage container industry. In such areas, the opportunity to use plastic containers is primarily for multiple use containers.

While plastic containers have perceived advantages over glass containers, such as weight and convenience, a perceived disadvantage of reusing plastic containers has been the potential for absorption of certain contaminants into the container walls after the rare occurrence of container misuse by a consumer. These absorbed contaminants have the potential to be desorbed back into the beverage when the container is refilled. Thus, the present process provides a means of identifying certain contaminants that are present on the container walls or that have been absorbed into he container walls.

Generally, conventional container inspection systems were developed for glass containers and were not concerned with absorption of contaminants into the container walls. These conventional systems are typically used for detecting the presence of solid particles or for the detection of contaminants in product-filled containers. For example, see U.S. Pat. Nos. 4,376,951 to Miyazawa, 4,551,627 to Wriech, 4,221,961 to Peyton, 4,087,184 to Knapp et al., 4,083,691 to McCormack et al, 3.966,332 to Knapp et al, and 4,459,012 to Wriech et al.

However, the present invention provides a novel process for detecting contaminants which are present on or have been absorbed into the walls of plastic containers. Moreover, this invention provides a process which is commercially viable for inspecting and reusing plastic containers in the beverage industry.

SUMMARY OF THE INVENTION

The present invention provides a process for detecting organic contaminants which are present on or absorbed into the walls of plastic containers comprising:

(a) injecting a substantially inert gas into the (b) drawing a vapor sample from within the container, (c) analyzing the sample by ionization techniques to detect the presence of contaminants in the container.

Also provides is an apparatus for practicing the process of the present invention.

BRIEF DESCRIPTION OF THE DRAWINGS

One embodiment of the present invention is more fully understood with reference to the following illustration wherein.

DETAILED DESCRIPTION OF THE INVENTION

Figure 1:
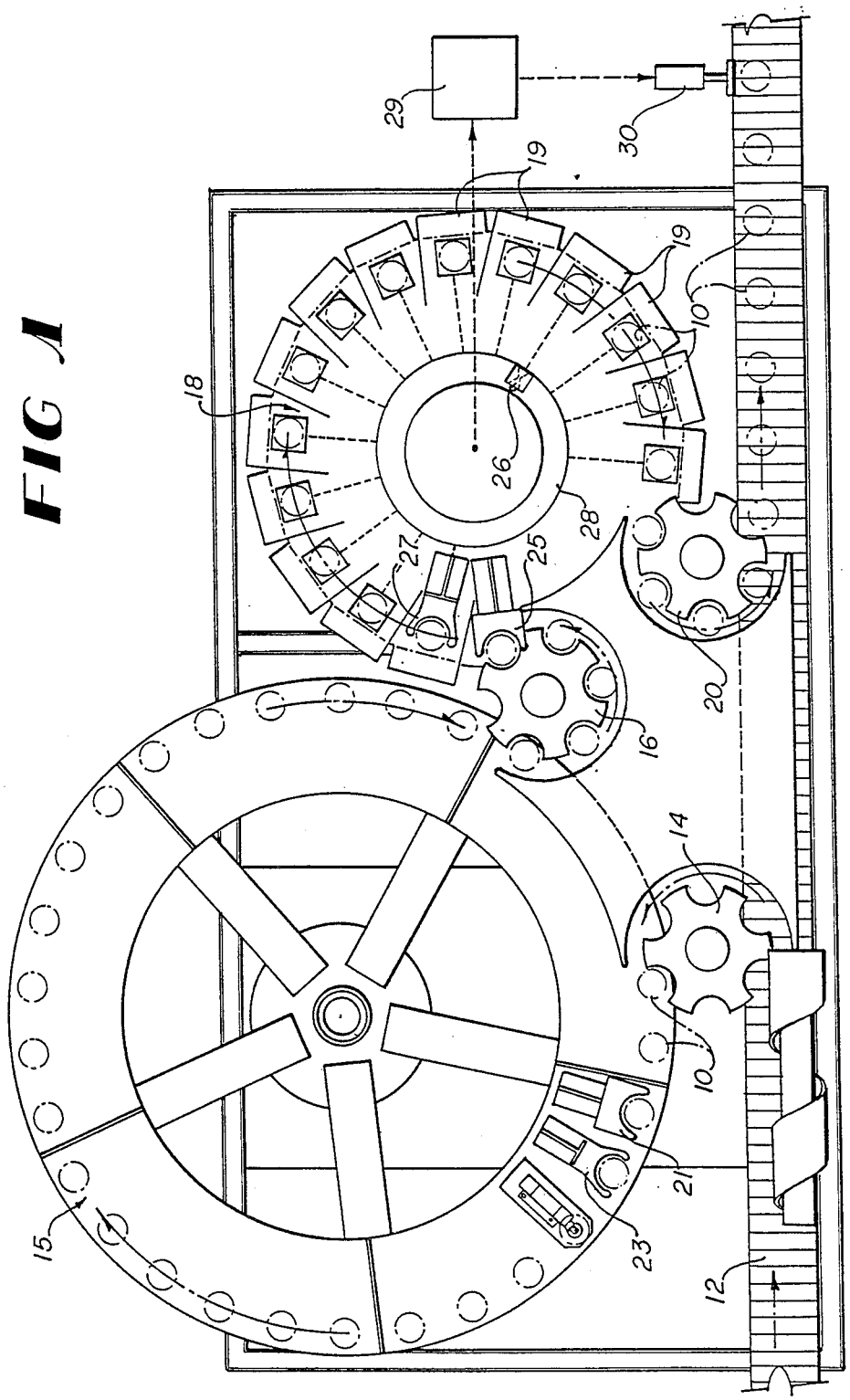
FIG. 1 is a top view showing a preferred method for practicing the process of the present invention.

The process of the present invention employs the surprising discovery that the persistence of organic contaminant volatility as compared to the beverage residue volatility provides a technique for the detection of contaminants presence in reusable plastic containers and particularly plastic bottles. In other words, it has been discovered that the volatiles derived from the beverage residue are not released at the same rate or to the same extent as the volatiles derived from the residue of organic contaminants. When all of the initial volatiles have been removed from the container, the volatiles from the contaminant residue are again released or released more rapidly and are therefore detectable from and distinguished from the volatiles derived from the beverage residue. Thus, this discovery can be employed to discriminate between the volatiles derived from the organic contaminants from the volatiles derived from the beverage residue and hence, the detection of organic contaminants present in the walls of plastic containers.

According to the present process, empty plastic containers which have been returned after use are inspected for contamination by a) removing all volatiles from within the container by injecting a substantially inert gas into the container, b) drawing a sample of the newly formed vapors from within the container and c) analyzing the sample by ionization means to determine the total ionizables present. It is preferred that the present process be employed prior to washing the containers.

Plastic containers as used herein include containers made from any suitable polymer, copolymer or resins useful for food contact applications. Examples of such materials include but are not limited to PET, polyvinyl chloride, and polycarbonate.

The gas employed herein can be injected into the container using any of the well known techniques for accomplishing such an objective. For example, any suitable gas injection tube or nozzle can be inserted into the container from the opened dispensing end or neck. The nozzle should leave a space or outlet for the volatiles from within the container to be vented into the atmosphere. Typically, the nozzle is a cylindrical tube having an inside diameter corresponding to about 10% to about 80% of the inside diameter of the mouth of the container. Generally, the nozzle will be inserted into the container to a point from about 0.5 to about 7.0 inches (about 1.25 cm to about 18.0 cm) from the top of the container depending on the container size. Although one injection is preferred, multiple injections of the gas may be used to remove the volatiles from the container.

The gas used in accordance with this invention can be any substantially inert gas that will not adversely affect the contaminant detection means by providing false readings. Suitable gases include nitrogen, helium, argon, carbon dioxide, air and the like. Preferably, air which is substantially free from contaminants is used because of its lower cost.

The duration, temperature and pressure employed for the gas injection depends on the particular gas utilized. For example, it is preferred that the duration of each gas injection be from about 1 to about 15 seconds. The pressure may vary from about 20 psig (about 1.4 kg/sq. cm. gage) to about 100 psig (about 7.0 kg/sq. cm. gage) and preferably is about 75 psig (about 5.3 kg/sq. cm. gage) when using air. The gas temperature can vary from about 10° C. to about 50° C., but it is preferably ambient (about 20° C.). The linear velocity is established by the pressure ratio to obtain critical flow. Typically, the linear velocity is between about 1000 and about 5000 feet per second. The gas displacement volume is generally from about 100% to about 1500% of the volume capacity of the container.

Once the volatiles are remove from the containers, samples of the newly formed vapors are drawn. Generally, the samples can be drawn utilizing conventional pumps, venturi devices or blowers with or without a vacuum accumulator or vacuum cylinder. It is preferred to seal the container when drawing the sample in order to ensure that no contaminants from the atmosphere will enter the ignition chamber of the ionization instrument. Partial sealing is possible if the surrounding air is substantially free of airborne contaminants. Depending upon the condition of the surrounding air of the testing area and of the container facility in general, one or more fans, blowers, or the like may be used to move the air surrounding the testing area away from the testing equipment or to keep fresh, clean air circulating through the testing area. This helps to decrease the likelihood of false readings occurring from airborne contaminants. Conventional industrial fans have been found suitable for this purpose.

The vapor samples drawn from the containers are preferably analyzed by ionization techniques to identify the total ionizables present (TIP). A TIP reading, which is in excess of the established TIP reading for uncontaminated containers indicates organic contaminants have been placed in the container. A standard TIP reading can be determined by simply testing an uncontaminated container in the environment in which the process is to be used.

Suitable ionization techniques include flame ionization (including laser-enhanced flame ionization) and photoionization with the photoionization including ultraviolet photoionization. It is preferred to use ultraviolet (UV) photoionization wherein the vapor samples are passed over a ultraviolet lamp. Such photoionization techniques, including ultraviolet photoionization techniques are known in the art. One advantage to using ionization techniques is that it has been found that the ionization of the vapor sample produces an electric current flow that is proportional to the amount of contamination. Thus, ionization allows for a quantitative reading of TIP.

While ionization techniques are the preferred mode for analyzing the presence of contaminants herein, contemplated equivalent analytical techniques include the various mass spectrometry techniques which separate and identify ions by their mass. Such mass spectrometry techniques are believed to be capable of application in the present process and are intended to be included herein.

The present invention is directed to detecting contaminants which are generally undetected by observation. Typically, these contaminants are organic compounds found in chemical mixtures available to consumers such as in cleaning agents, gasoline, motor oil, kerosene, paint thinner or the like and which have been placed into the container by the consumer for storage or other purposes.

The detectable compounds of this invention cover a wide range of organic compounds and include chemical mixtures containing one or more of these compounds. Typically, these organic compounds are used as solvents in commercial chemical mixtures but are not limited to such uses.

Preferably, the present process can be employed to detect hydrocarbons, alcohols, ketones or mixtures containing one or more of these compounds. Specifically included are chemical mixtures wherein the hydrocarbons, alcohols or ketones are present from trace amounts to 100% by volume. The present process is most preferably used to detect hydrocarbons.

Examples of such hydrocarbons include alkanes, alkenes, alkadienes, acetylenes, acyclic terpenes, cycloparaffins, cycloolefins, cycloacetylenes, aromatics, cyclic terpenes, and related petroleum derived hydrocarbons. Preferred hydrocarbons are alkanes, alkenes, aromatics and cyclic terpenes and most preferred are petroleum derived hydrocarbons.

Examples of alcohols detectable by the present process include monohydric alcohols; aliphatic, alicyclic, and aromatic; dihydric; trihydric; and polyhydric alcohols. The present process is preferably employed to direct alicyclic and aromatic alcohols.

The ketones detectable by the present process include all compounds having at least one carbonyl group and includes monoketones, polyketones and hycrocyclic ketones.

While the above lists have been included as way of example, it is believed that the present invention will detect all organic compounds or mixtures containing such compounds which may be present on or absorbed in the container walls. Thus, the above provided lists of compounds should not be used to limit the scope of this invention which shall include all organic compounds which are within the analytical capabilities of the detection equipment.

The contaminants which can be detected using the preferred photoionization analysis are organic compounds having an ionization potential of below about 11.2 eV or below about 10.6 eV depending solely on the light source employed in the photoionization instrument. This includes compounds having multiple components wherein at least one of the hydrocarbons or other organic compounds present have an ionization potential of below about 11.2 eV or about 10.6 eV. While light sources with the ability to ionize compounds having an ionization potential of 11.2 eV can be employed, those with an ionization potential of 10.6 eV are commercially preferred because of their durability and decreased maintenance requirements. Of course, as new light sources are developed, a greater range of compounds will become commercially detectable without departing from the present invention.

Figure 2:
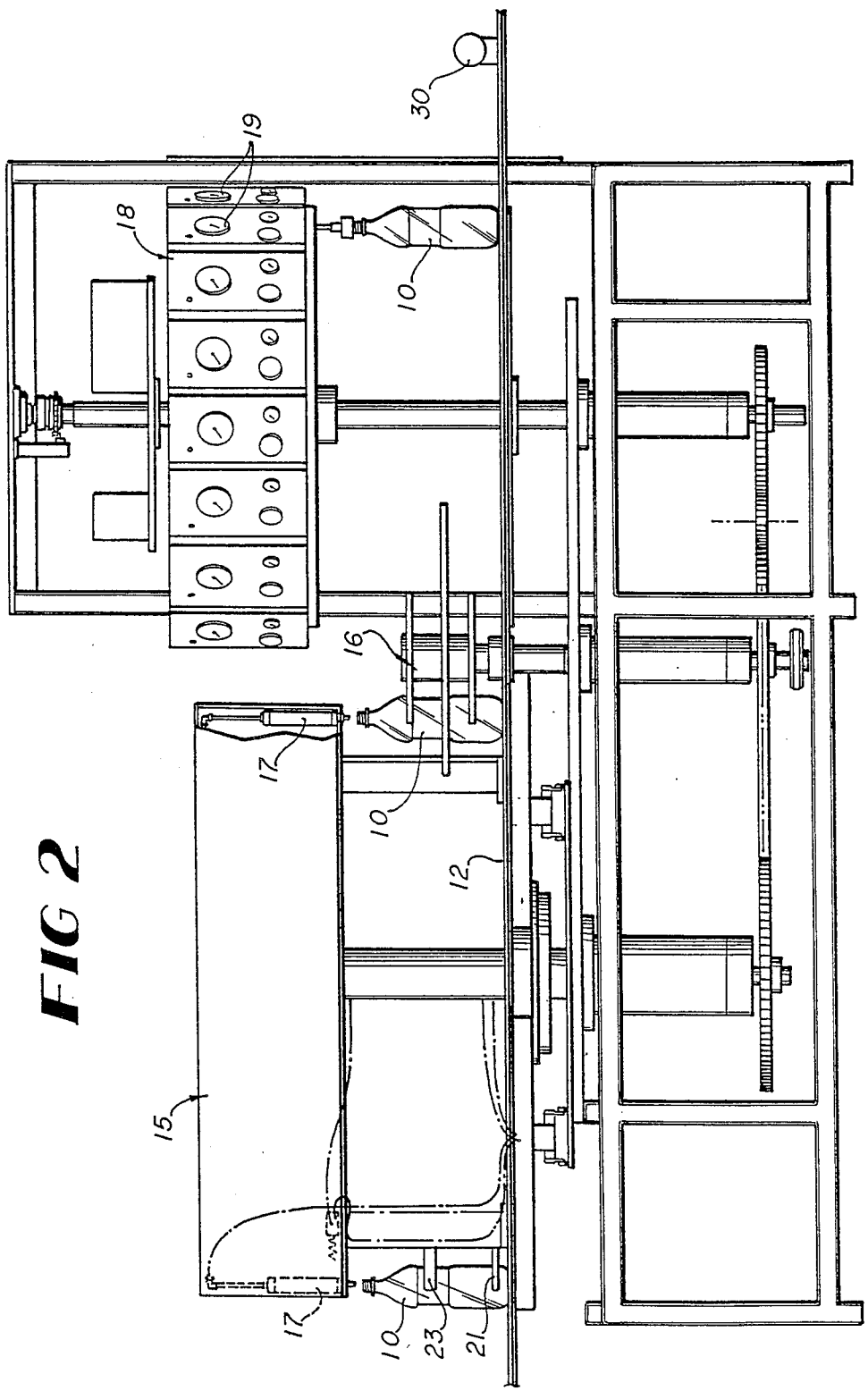
FIG. 2 is a side view of FIG. 1.

In a preferred embodiment of this invention as illustrated in FIG. 1, an in-line testing system is provided which can detect organic contaminants which have been placed in plastic containers. Referring to FIGS. 1 and 2, used plastic containers 10 are placed into an existing bottling line conveyor 12. The containers 10 are removed from conveyor 12 by a first transferring means 14 which accepts the containers 10 from the conveyor 12 and transfers them to a first rotaty disc 15. Rotary disc 15 has multiple nozzles 17 for injecting a substantially inert gas into the containers 10. The first rotary disc 15 has cradles 21 for aligning the containers 10 and grippers 23 for holding the containers 10 in place during the gas injections. The nozzles 17 are attached to a source of compressed gas and are positioned above each cradle 21 and inserted into the containers 10. The containers 10 are rotated around the disc 15 while receiving one or more injections of the gas employed by nozzles 17.

After the gas injection, the containers 10 are then transferred to a second rotary disc 18 by a second transferring means 16. The second rotary disc 18 has cradles 25 and grippers 27 at each station. Each station is connected to a vacuum accumulator 28 which is activated by a venturi 26. A vapor sample from each container 10 as the containers 10 are rotated around the second rotary disc 18. The vapor sample is transported to a UV photoionization instrument 19 which is positioned above each cradle 25. The UV photoionization instruments 19 analyze the vapor samples for the presence of total ionizables present in a conventional manner.

Preferably, the UV photoionization instruments 19 are connected to a microprocessor 29 which receives an electronic signal from the instruments 19 and sends an electronic signal to a rejection means 30. The microprocessor 29 receives the electronic signal representing the numerical reading from the photoionization instrument 19 for a particular container 10 and compares it against a predetermined value. If the reading is above or below the predetermined value, the microprocessor 29 sends a signal to the rejection means 30 to reject the container 10.

The containers 10 are transferred by a third transferring means 20 to the conveyor 12 after testing. The contaminated containers are then rejected by the rejecting means 22 which is typically an air blast or air ram which physically removes the container 10 from the conveyor 12 as known in the art.

The transferring means 14, 16 and 20 are typically star wheels which are timed in sequence to systematically communicate with the rotary discs 15 and 18 and with the conveyor 12 and operate continuously. Such star wheels utilize known principles of operation and are currently used in the beverage industry.

SPECIFIC EMBODIMENTS

Test Procedure #1

In order to test for the contaminants by the present invention, multiple 1.5 liter PET bottles were prepared according to the following procedure. Each bottle was filled with orange soda sold under the trademark "Minute Maid" (a product of The Coca-Cola Company), capped, and stored for 24 hours. This beverage was used because preliminary tests indicated that it had the highest total ionizables present of the board range of carbonated beverages tested thereby making it the most severe case. The bottles were then opened and the beverage was removed. The empty bottles were again capped and stored for one hour, seven days and fourteen days respectively. After storage,each bottle was uncapped and tested before injecting air by drawing a vapor sample and analyzing the sample with a UV photoionization instrument. The bottles were then treated by injecting five separate injections of a duration of one second of ambient air into each bottle at 40 psig, drawing a vapor sample, and analyzing the samples with a UV photoionization instruments. The photoionization instruments were commercially purchased from Photovac, Inc. The UV photoionization instrument had a continuous voltage source of 12.0 Vdc with ±0.2 output and was frequently calibrated against a 100 ppm isobutylene (in air) standard gas. The UV lamp crystal in the UV photoionization instrument was cleaned frequently and the inlet filters were changed on daily basis. The instrument reading indicates total ionizables present (TIP) by reference to the isobuylene. Representative results are shown in Table I.

Test Procedure #2

The second test procedure was similar to test procedure #1 except that after a 24 hour storage of the beverage, various contaminants were placed into the empty containers. The contaminants were left in the containers for 14 days, emptied, and the containers were stored with closures. Ionization readings were taken at various time intervals. Representative results are shown in Table II (see "with closures").

Test Procedure #3

The third test procedure was identical to test procedure #2 except that the beverage was not placed into the containers and that the containers were stored without closures prior to testing. The results are shown in Table III (see "without closures"). Results The results as shown in Table I, II and III indicate that contaminants having an ionization potential below about 10.6 eV (the limitations of the UV light source) can be reproducible detected in reused plastic containers using the process of the present invention. In each test, the beverage residue volatiles did not affect the contaminant reading even though the beverage, residue containers had a high TIP reading when test alone. As shown in Table I, the volatiles of the beverage residue can be totally removed using the gas injection pretreatment. However, as shown in Tables II and III, the volatiles from the contaminant residue continue to appear and give high TIP reading even after the gas pretreatment.

Not intending to be bound to theory, it is believed that the pretreatment described in this invention, removes the volatiles associated with the beverage residue due to the air turbulance or scrubbing action from the gas injection pretreatment. The elimination or reduction of volatility of any remaining beverage residue after pretreatment with gas injections greatly reduces or eliminates the possibility of registering a TIP reading that would result in the rejection of the container as containing contaminant. The volatility of the organic contaminants persist after the gas injections and those contaminants that are present on or absorbed in the plastic container walls are detected as evidenced by the TIP reading as compared to the standard TIP reading for a clear container.

It is to be understood that the present invention is not to be limited by the drawings or the embodiments set forth herein which have been provided merely to demonstrate operability. Modifications, variations and equivalent embodiments can be employed without departing from the spirit and scope of this invention.

TABLE I

DETECTION FOR TOTAL IONIZABLES
PRESENT (TIP) FROM BEVERAGE RESIDUE*

| STORAGE TIME | NO. OF SAMPLES | TIP READING RANGE BEFORE | AFTER |
|---|---|---|---|
| 1 hour | 21 | 98 to 141 | −3 to −8 |
| 7 days | 21 | 5 to 15 | −1 to −3 |
| 14 days | 20 | 2 to 19 | −4 to −5 |

*All tests used orange soda sold under the Trademark "MINUTE MAID" (a registered trademark of The Coca-Cola Company) using 5 air injections of 1 second duration at 40 psig.

TABLE II

DETECTION FOR TOTAL IONIZABLES
PRESENT (TIP) FROM CONTAMINANT RESIDUE

| CONTAMINANT | CONCENTRATION | DAYS STORED | TIP READINGS WITH CLOSURES |
|---|---|---|---|
| Acetone | 100% | 1 | 2000 |
|  |  | 10 | 2000 |
|  |  | 25 | 2000 |
| Gasoline | 100% | 1 | 2000 |
|  |  | 10 | 1600 |
|  |  | 25 | 1000 |
| Diesel Fuel | 100% | 1 | 2000 |
|  |  | 10 | 2000 |
|  |  | 25 | 1030 |
| Kerosene | 100% | 1 | 2000 |
|  |  | 10 | 2000 |
|  |  | 25 | 1390 |
| Isopropanol | 100% | 1 | 420 |
|  |  | 10 | 600 |
|  |  | 25 | 270 |
| Motor Oil (clean) | 100% | 1 | 90 |
|  |  | 10 | 90 |
|  |  | 25 | 20 |

TABLE III

DETECTION FOR TOTAL IONIZABLES
PRESENT (TIP) FROM CONTAMINANT RESIDUE

| CONTAMINANT | CONCENTRATION | DAYS STORED | TIP READINGS WITHOUT CLOSURES |
|---|---|---|---|
| Acetone | 100% | 1 | 767 |
|  |  | 3 | 27 |
|  |  | 7 | 10 |
| Diesel Fuel | 100% | 1 | 144 |
|  |  | 3 | 89 |
|  |  | 7 | 86 |
| Gasoline | 100% | 1 | 532 |
|  |  | 3 | 269 |
|  |  | 7 | 94 |
| Isopropanol | 100% | 1 | 201 |
|  |  | 3 | 192 |
|  |  | 7 | 182 |
| Kerosene | 100% | 1 | 836 |
|  |  | 7 | 274 |
| Motor Oil (used) (trace gasoline) | 100% | 1 | 341 |
|  |  | 3 | 129 |
|  |  | 7 | 86 |

What is claimed is:

1. A process for detecting volatile contaminant components of organic contaminants which are present on or absorbed into the walls of plastic containers having a beverage residue including volatile beverage components comprising:

(a) injecting a substantially inert gas into said containers to remove the volatile beverage components and volatile contaminant components, (b) drawing a vapor sample after the release of additional volatile contaminant components by the organic contaminant but before any substantial release of volatile beverage components by the beverage residue, and (c) analyzing said sample by ionization means to detect the presence of the volatile contaminat components in said container.

2. The process of claim 1 wherein said gas is injected at a pressure from about 20 psig to about 100 psig, a temperature from about 10° C. to about 50° C. and for a duration of from about 1 to about 15 seconds.

3. The process of claim 2 wherein said gas is selected from the group consisting of nitrogen, helium, argon, carbon dioxide, and air which is substantially free of contaminants.

4. The process of claim 3 wherein said gas is air which is substantially free of contaminants.

5. The process of claim 4 wherein said injections are at a linear velocity of between about 1000 feet per second to about 5000 feet per second.

6. The process of claim 1 wherein said containers are PET bottles.

7. The process of claim 1 wherein said organic contaminants have an ionization potential of below above 10.6 eV.

8. The process of claim 1 wherein said ionization means is ultraviolet photoionization.

9. The process of claim 1 wherein said organic contaminants are selected from hydrocarbons, alcohols, ketones or mixtures thereof.

10. The process of claim 11 wherein said organic contaminants are hydrocarbons.

11. A process for detecting the presence of volatile contaminant components of organic contaminants which are present on or absorbed into the walls of plastic containers having a beverage residue including volatile beverage components, said process comprising the sequential steps of:

(a) injecting one or more injections or ambient air into said containers whereby the volatile beverage components and the volatile contaminant components are removed, (b) drawing a vapor sample from within said container after the release of additional volatile contaminant components by the organic contaminant but before any substantial release of volatile beverage components by the beverage residue, (c) analyzing said sample by photoionization means to obtain a numerical value for total ionizables present in said container, and (d) comparing said numerical value against a predetermined numerical value for uncontaminated containers.

12. The process of claim 11 wherein said containers are rejected when said numerical value of any of said containers is above or below said predetermined numerical value.

13. The process of claim 12 wherein the comparison between said numerical value and said predetermined numerical value is performed by a microprocessor.

* * * * *